(12) United States Patent
Kim et al.

(10) Patent No.: US 10,857,119 B2
(45) Date of Patent: Dec. 8, 2020

(54) COMPOSITION CONTAINING MONOACETYLDIACYLGLYCEROL COMPOUND AS ACTIVE INGREDIENT FOR INHIBITING BLOOD CANCER OR METASTASIS

(71) Applicants: ENZYCHEM LIFESCIENCES CORPORATION, Daejeon (KR); KOREA RESEARCH INSTITUTE OF BIO SCIENCE AND BIOTECHNOLOGY, Daejeon (KR)

(72) Inventors: Jae Wha Kim, Daejeon (KR); Sei-Ryang Oh, Daejeon (KR); Kyung Seop Ahn, Daejeon (KR); Ho Bum Kang, Daejeon (KR); Jae Min Shin, Daejeon (KR); Young Eun Ko, Daejeon (KR); Tae Suk Lee, Daejeon (KR); Myung Hwan Kim, Seoul (KR); Jong Koo Kang, Chungcheongbuk-do (KR); Yong-Hae Han, Seoul (KR); Ki-Young Sohn, Seoul (KR)

(73) Assignees: Enzychem Lifesciences Corporation, Englewood Cliffs, NJ (US); Korea Research Institute of Bio Science and Biotechnology, Daejeon (KR)

( * ) Notice: Subject to any disclaimer, the term of this patent is extended or adjusted under 35 U.S.C. 154(b) by 0 days.

(21) Appl. No.: 16/045,617

(22) Filed: Jul. 25, 2018

(65) Prior Publication Data
US 2019/0022047 A1 Jan. 24, 2019

Related U.S. Application Data

(63) Continuation of application No. 14/912,916, filed as application No. PCT/KR2014/007620 on Aug. 18, 2014, now Pat. No. 10,058,527.

(30) Foreign Application Priority Data

Aug. 19, 2013 (KR) .......................... 10-2013-0098185

(51) Int. Cl.
| | | |
|---|---|---|
| A61K 31/231 | (2006.01) |
| A61K 31/23 | (2006.01) |
| A23L 33/10 | (2016.01) |
| A61K 35/32 | (2015.01) |
| A61K 31/22 | (2006.01) |

(52) U.S. Cl.
CPC ............ *A61K 31/231* (2013.01); *A23L 33/10* (2016.08); *A61K 31/23* (2013.01); *A61K 35/32* (2013.01); *A23V 2002/00* (2013.01); *A61K 31/22* (2013.01)

(58) Field of Classification Search
CPC ...................................................... A61K 31/22
USPC ......................................................... 514/547
See application file for complete search history.

(56) References Cited

U.S. PATENT DOCUMENTS

| | | | |
|---|---|---|---|
| 7,662,853 B2 | 2/2010 | Kim | |
| 10,058,527 B2 * | 8/2018 | Kim | ........................ A61K 31/23 |
| 2008/0200543 A1 | 8/2008 | Kim | |
| 2009/0253923 A1 | 10/2009 | Lee et al. | |

FOREIGN PATENT DOCUMENTS

| | | |
|---|---|---|
| KR | 10-1999-0044781 A | 6/1999 |
| KR | 10-2005-0103259 A | 10/2005 |
| KR | 10-2006-0047447 A | 5/2006 |
| KR | 10-2007-0010841 A | 1/2007 |
| WO | 99/26640 A1 | 6/1999 |
| WO | WO-2005112912 A1 * | 12/2005 ............. A61K 31/22 |

OTHER PUBLICATIONS

International Preliminary Report on Patentability and Written Opinion of the International Search Authority with English translation, dated Feb. 23, 2016, for Application No. PCT/KR2014/007620.
Kim, Myung-Hwan, et al., "EC-18, a synthetic monoacetyldiglyceride, inhibits hematogenous metastasis of KIGB-5 biliary cancer cell in hamster model", Journal of Korean Medicine, vol. 24, (2009) 474-480.
English language summary of Office Action in Chinese counterpart Application No. 2014800552912 (1 page).
Office Action issued in counterpart India Application No. 20167009591 (5 pages).
English language summary to Japanese Office Action dated Jul. 3, 2017 issued in counterpart Japanese Application 2016-536021.
Examination report issued in counterpart European application 14 838 256.7.
Kim, Myung-Hwan, et al. "EC-18, a synthetic monacetyldiacylglyveride, inhibits hematogenous metastasis of KIGB-5 biliary cancer cell in hamster model." Journal of Korean medical science 24.3 (2009): 474-480.

\* cited by examiner

Primary Examiner — Kevin E Weddington
(74) Attorney, Agent, or Firm — Mintz Levin Cohn Ferris Glovsky and Popeo, P.C.; Peter F. Corless

(57) ABSTRACT

The present invention relates to a composition containing a monoacetyldiglyceride compound as an active ingredient, for inhibiting blood cancer or metastasis, and a use thereof. The monoacetyldiglyceride compound according to the present invention has excellent effects of inhibiting the expression of IL-4 and inhibiting the activity of STAT-6, and thereby is capable of overcoming side effects of currently used blood cancer or metastasis inhibiting agents. Also, the monoacetyldiglyceride compound is a non-toxic compound having superior therapeutic effects and thus can be useful as a composition for preventing, treating, or improving blood cancer and metastasis.

23 Claims, 7 Drawing Sheets
Specification includes a Sequence Listing.

[FIG. 1]
A.
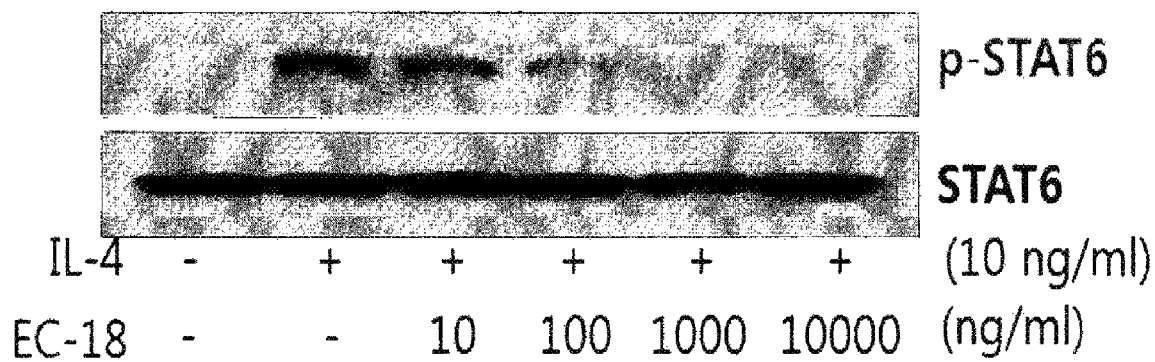
B.
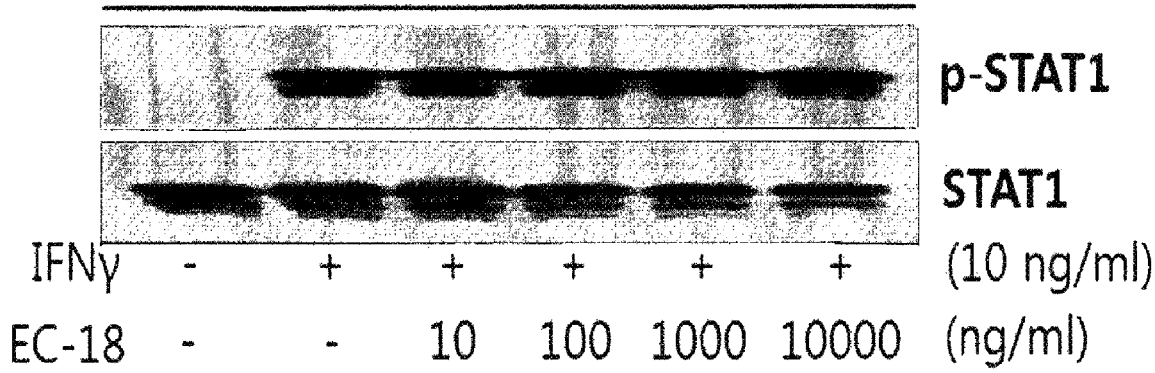

[FIG. 2]
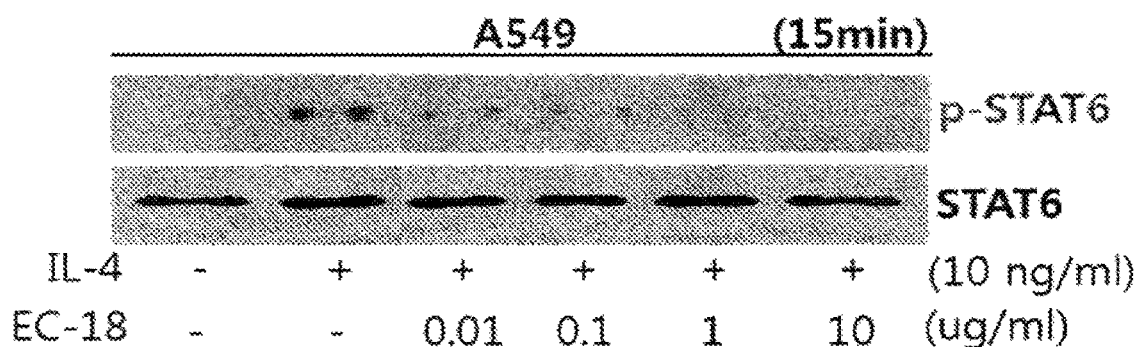
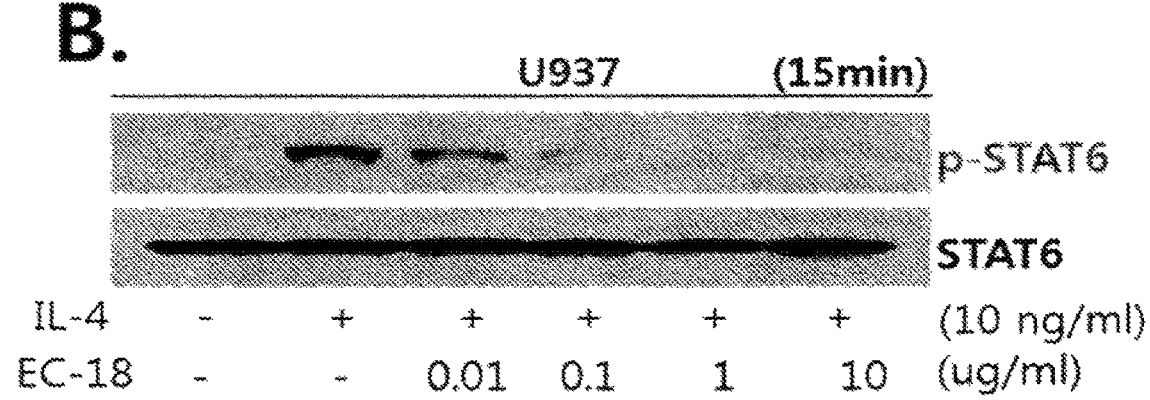
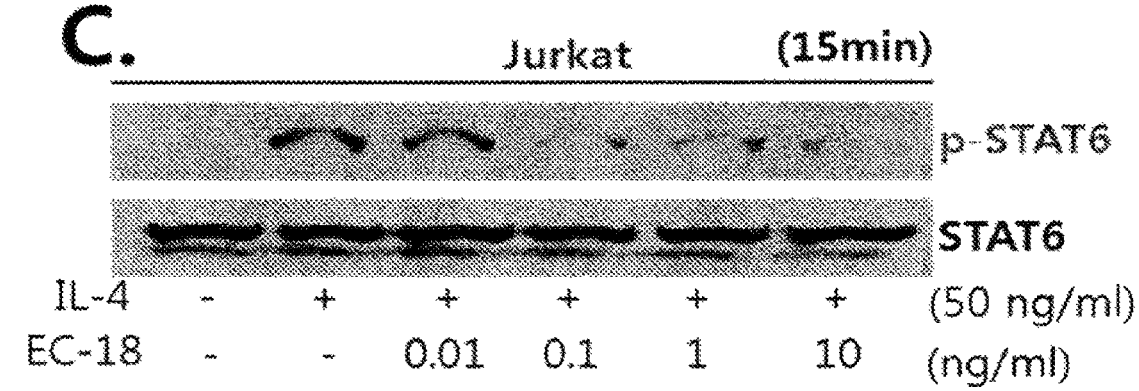

[FIG. 3]
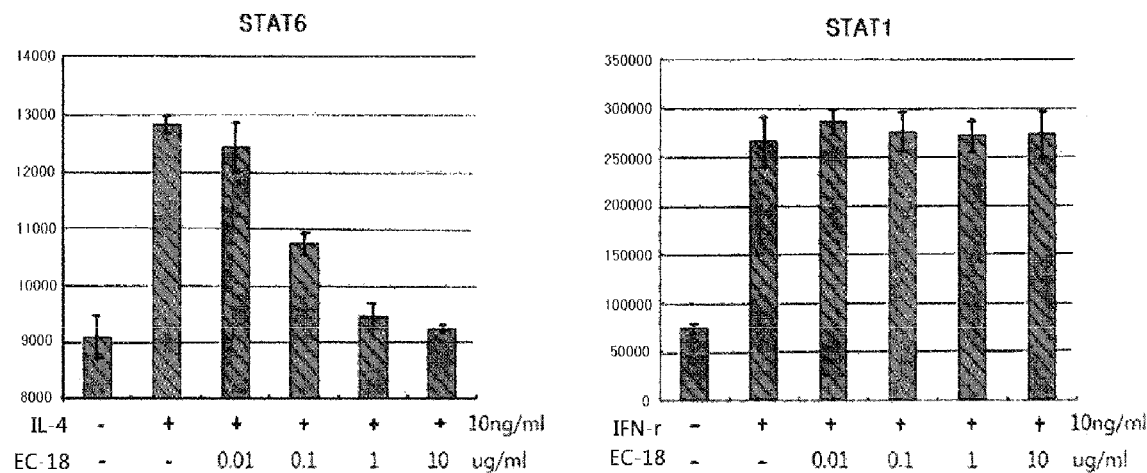
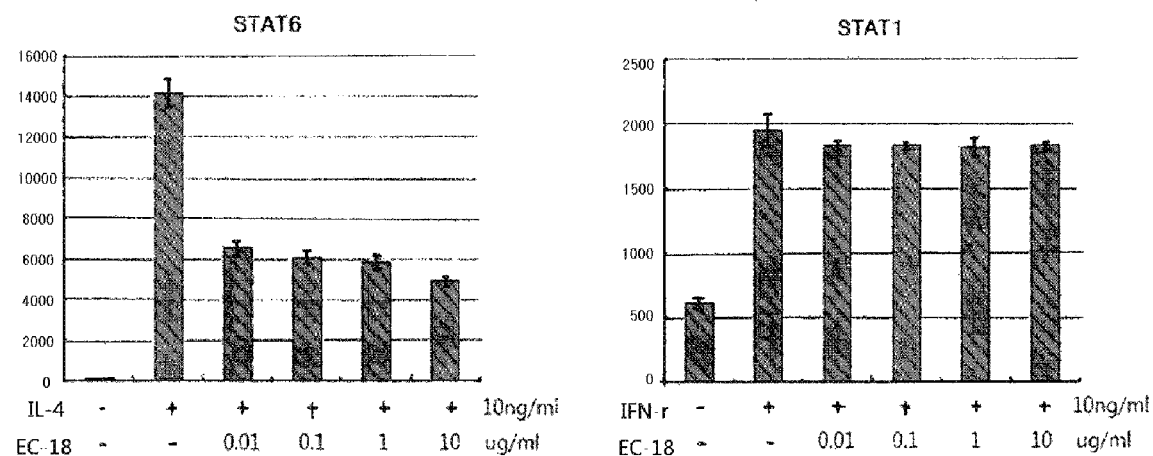

[FIG. 4]
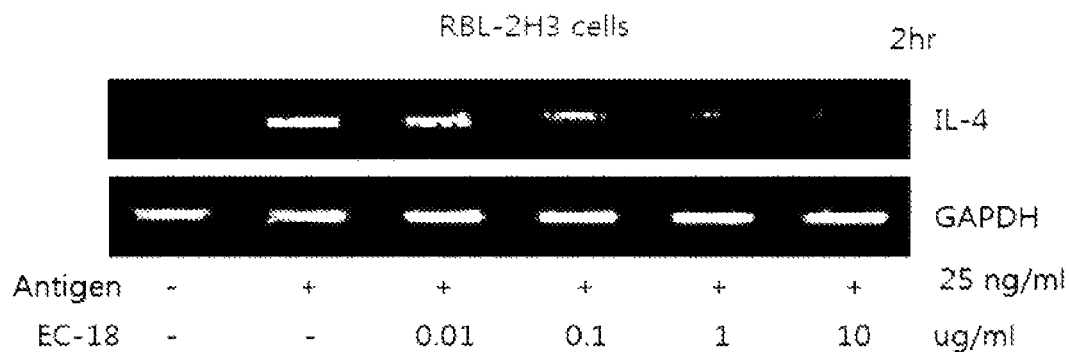
[FIG. 5]
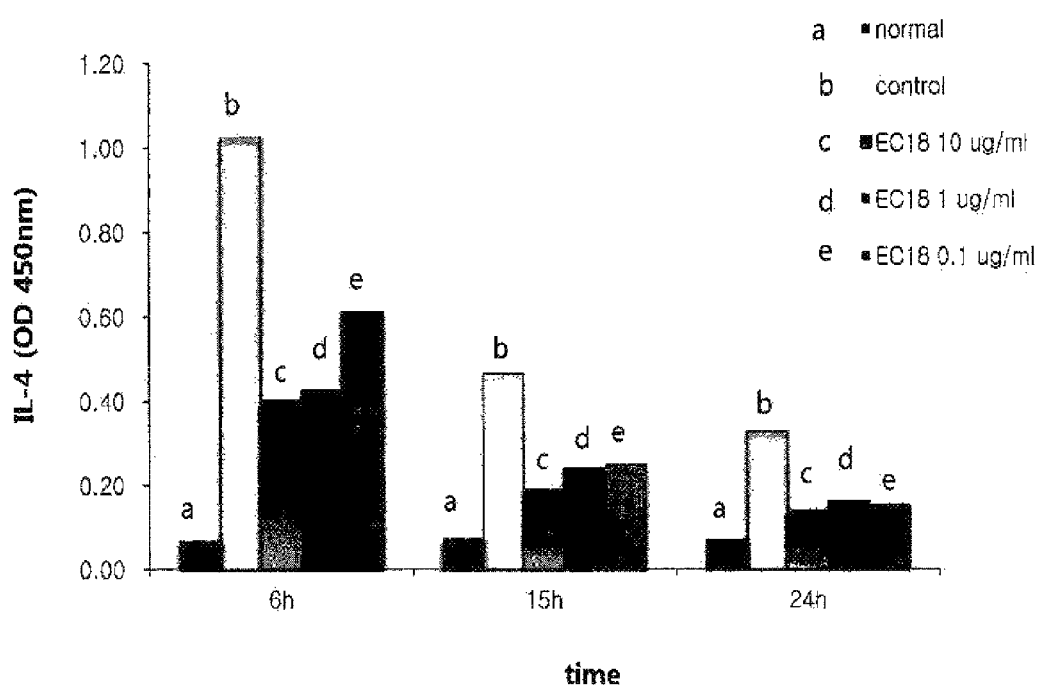

[FIG. 6]
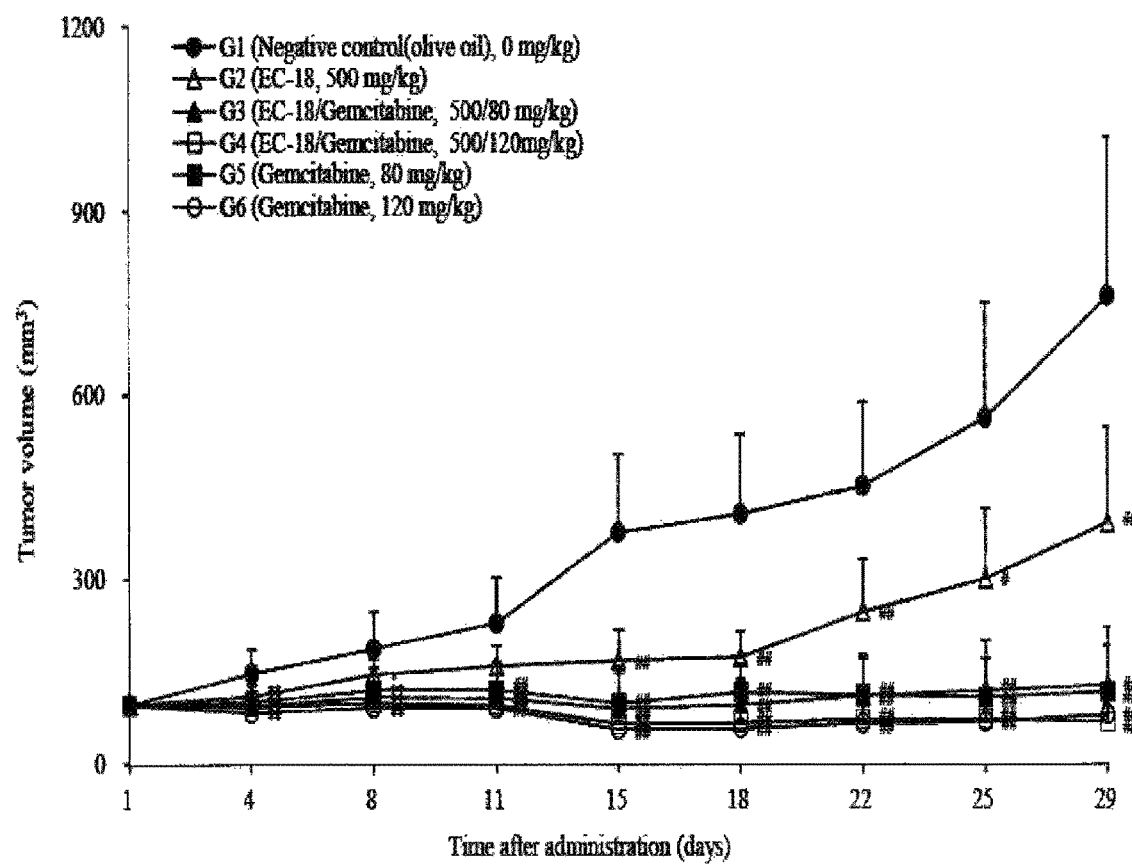

[FIG. 7]
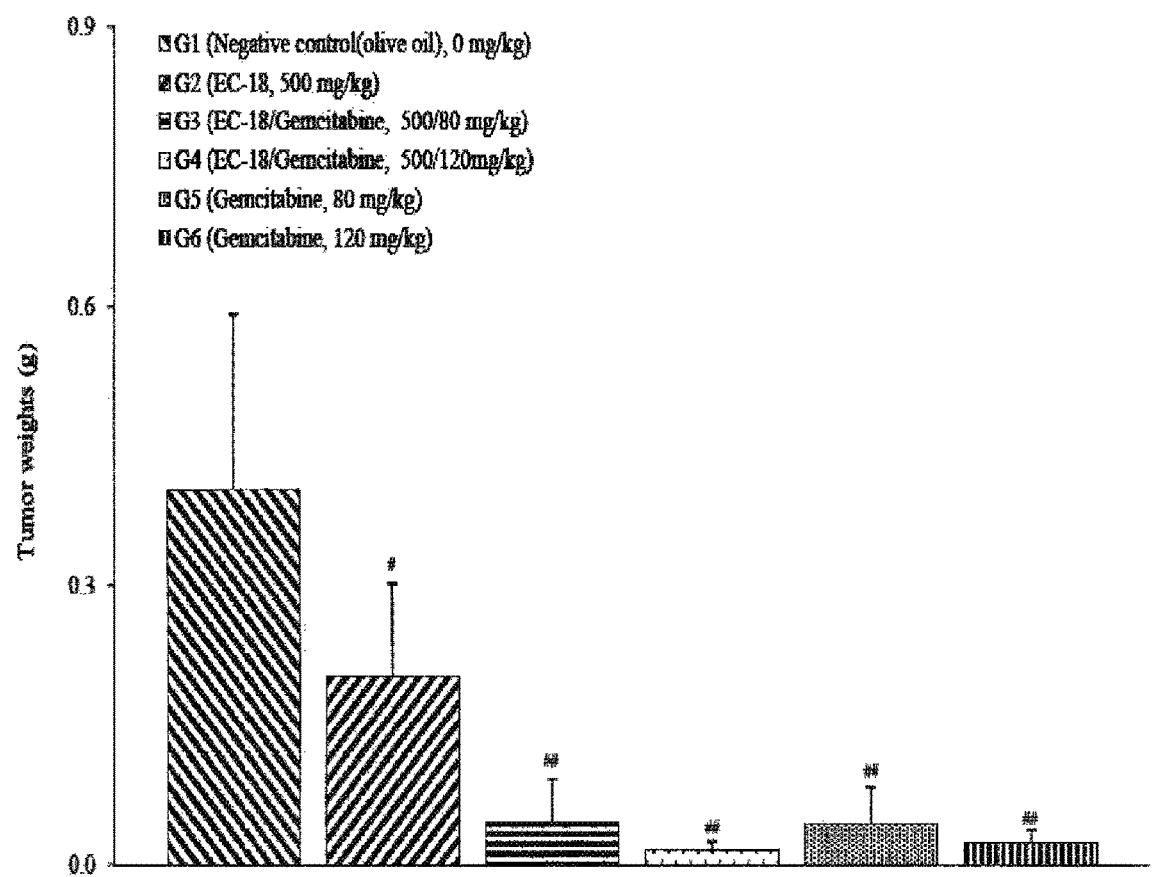

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: GAPDH forward primer

```
<400> SEQUENCE: 1
ccatcaccat cttccaggag                                              20

<210> SEQ ID NO 2
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 2
acagtcttct gggtggcagt                                              20

<210> SEQ ID NO 3
<211> LENGTH: 20
<212> TYPE: DNA
<213> ORGANISM: Artificial Sequence
<220> FEATURE:
<223> OTHER INFORMATION: IL-4 forward primer

<400> SEQUENCE: 3
aatgggtctc acctcccaac                                              20

<210> SEQ ID NO 4
<211> LENGTH: 20
<212> TYPE: DNA
<213> ORGANISM: Artificial Sequence
<220> FEATURE:
<223> OTHER INFORMATION: IL-4 reverse primer

<400> SEQUENCE: 4
ttcagctcga acactttgaa                                              20
```

COMPOSITION CONTAINING MONOACETYLDIACYLGLYCEROL COMPOUND AS ACTIVE INGREDIENT FOR INHIBITING BLOOD CANCER OR METASTASIS

This Application is a Continuation of Application of 14/912,916 filed on Feb. 18, 2016 which is a national entry of International Application PCT/KR2014/007620 which claims priority from Application 10-2013-0098185 filed on Aug. 19, 2013 in the Republic of Korea. The entire contents of these applications are incorporated herein by reference in their entirety.

REFERENCE TO A SEQUENCE LISTING

The Sequence Listing written in file 055312-512C01US_ST25.txt, created on Oct. 4, 2018, 1,311 bytes, machine format IBM-PC, MS-Windows operating system, is hereby incorporated by reference.

TECHNICAL FIELD

The present invention relates to a composition for inhibiting blood cancer or metastasis, comprising a monoacetyldiglyceride compound as an active ingredient, and a use thereof.

BACKGROUND ART

Cancer, which is also referred to as a tumor, means groups of abnormal cells which are generated by unlimitedly continued fragmentation and proliferation of cells, originating from destruction of the balance between cell division and apoptosis by a variety of causes. In general, cancers are expressed in various parts of the body more than 100 parts, including organs, white blood cells, bones, lymph nodes, etc, and then are developed into severe symptom through infiltration into the surrounding tissue and transition to a different organ. The causes of cancer include environmental or external factors such as the chemical, viral, bacterial, ionizing radiation and so on and internal factors such as congenital gene mutations and so on. Interest in the relation between chronic inflammation and cancer has been recently newly appeared and many data demonstrating the relation between the chronic inflammation and cancer has been reported. Infection and chronic inflammation occupy 25% of all cancer cause and it has been known that cancer risk is much higher in patients having chronic inflammation and ROS (Reactive Oxygen Species)-associated diseases. It is speculated that a variety of mediators that regulate the inflammatory response, that is, cytokine, free-radical, growth factor, etc. induce genetic, epigenetic changes such as mutations in tumor suppressor genes, DNA methylation, post-transcriptional modification, etc., change the route essential for maintaining cell homeostasis, and further generate and develop cancer.

If cancers are found in the initial, medical treatment such as radiation therapy or chemotherapy etc can be applied to the patients. However, the side effect of the medical treatment becomes a big problem. If cancers are found in the terminal or in the metastasis state, the patients should dwell in life-limiting condition without special treatment. Therefore, the research has been conducted for developing anti-cancer agent or cancer metastasis inhibitor having less side effect and great efficacy from low-toxic natural products, as a new approach for the cancer treatment. It had been found that the treatment originating in the natural products reduces the side effect of the suppression of hematopoiesis and immune function which is often observed in chemotherapy and radiation therapy.

EC-18, as a kind of monoacetyldiglyceride compounds, was separated or extracted from the natural deer antler. It is known that EC-18 increases survivability ratio of animals in sepsis animal model experiment using cecal-ligation-puncture, and shows no-toxicity in GLP (Good Laboratory Practice) toxicity test. However, the effect of monoacetyldiacylglycerol compounds including EC-18 is not known or disclosed in the blood cancer or cancer metastasis. Thus the present inventors aimed to find a compound derived from natural products or a novel compound for the inhibitor of blood cancer or cancer metastasis and found that the monoacetyldiacylglycerol compound inhibits IL-4 secretion and STAT-6 activation to destroy micro-environment for the growth of the cancer tissue and can be used to prevent or treat blood cancer or inhibit cancer metastasis.

DISCLOSURE

Technical Problem

It is an object of the present invention to provide a pharmaceutical composition and a health functional food containing a monoacetyldiacylglycerol compound represented by following Formula 1 as an active ingredient for inhibiting blood cancer or cancer metastasis.

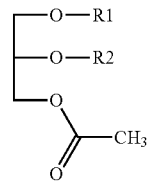

[Formula 1]

wherein R1 and R2 are independently a fatty acid residue of 14 to 22 carbon atoms.

It is an object of the present invention to provide a method for preventing or treating blood cancer or a method for inhibiting cancer metastasis comprising a step of administering the above composition to a subject suspicious of having blood cancer attack or cancer metastasis, or suffering from blood cancer.

Technical Solution

In an example to achieve the these and other objects, the present invention provides a pharmaceutical composition and a health functional food containing a monoacetyldiacylglycerol compound represented by following Formula 1 as an active ingredient for inhibiting blood cancer or cancer metastasis.

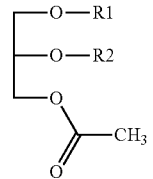

[Formula 1]

wherein R1 and R2 are independently a fatty acid group of 14 to 22 carbon atoms. In the Specification, the fatty acid group means the carboxyl group of fatty acids from which —OH group is extracted.

In detail, the pharmaceutical composition for inhibiting blood cancer or cancer metastasis according to the present invention includes a monoacetyldiacylglycerol compound represented by the Formula 1. In the present invention, the term "monoacetyl diacyl glycerol compound" means glycerol compounds having one acetyl group and two acyl groups, and can be referred as "monoacetyl diacyl glycerol (MADG)".

In the monoacetyl diacyl glycerol compound of Formula 1, R1 and R2 are independently a fatty acid residue of 14 to 22 carbon atoms. Preferably, non-limiting examples of R1 and R2 include palmitoyl, oleoyl, linoleoyl, linolenoyl, stearoyl, myristoyl, arachidonoyl, and so on. Preferable combinations of R1 and R2 (R1/R2) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In optical activity, the monoacetyl diacyl glycerol compound of Formula 1 can be (R)-form, (S)-form or a racemic mixture.

In one embodiment, the monoacetyl diacyl glycerol compound is a compound of the following Formula 2.

[Formula 2]

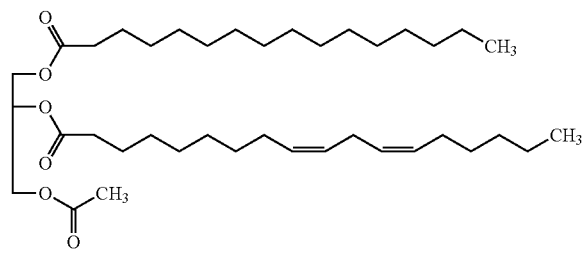

The compound of Formula 2 is 1-palmitoyl-2-linoleoyl-3-acetylglycerol, sometimes referred as "EC-18" in this specification. R1 and R2 of the compound of Formula 2 are palmitoyl and linoleoyl, respectively.

The monoacetyldiacylglycerol compounds can be separated and extracted from the natural deer antler or can be produced by known organic synthesis methods (Korean Registered Patents No. 10-0789323). More specifically, deer antler is extracted with hexane, followed by extracting the residue with chloroform and removing the chloroform to provide chloroform extracts. The volume of the solvents for this extraction is just enough to immerse the deer antler. In general, about 4-5 liters of hexane and/or chloroform for 1 kg of deer antler is used, but not limited thereto. The extracts obtained by this method is further fractionated and purified using series of silica gel column chromatograph and TLC method to obtain the monoacetyldiacylglycerol compound for the present invention. A solvent for the extraction is selected among chloroform/methanol, hexane/ethylacetate/acetic acid, but not limited thereto.

A chemical synthetic method for the preparation of monoacetyldiacylglycerol compounds is shown in Korean Registered Patents No. 10-0789323. Specifically, the method comprises (a) a step of preparing 1-R1-3-protecting group-glycerol by adding a protecting group in the position 3 of 1-R1-glycerol; (b) a step of preparing 1-R1-2-R2-3-protecting group-glycerol by introducing R2 in the position 2 of the 1-R1-3-protecting group-glycerol; and (c) a step of preparing the desired monoacetyldiacylglycerol compound by performing a deprotection reaction and the acetylation reaction of the 1-R1-3-protecting group-glycerol at the same time. The monoacetyldiacylglycerol compound may be further purified if necessary. Alternatively, monoacetyldiacylglycerol compounds can be prepared by acid decomposition of phosphatidylcholine (acetolysis) but is not limited thereto. Stereoisomers of the compounds of formula (I) are also within the scope of the invention.

In the present invention it is shown that monoacetyldiacylglycerol compounds are capable of reducing the secretion of IL-4, and thus the monoacetyldiacylglycerol compounds can be effectively used for the suppression of the blood cancer or the cancer metastasis. \

In the present invention, the term "cancer" indicates a state that the abnormal cells which should be normally killed but alive and excessively proliferated by control disorder of cell itself, invade surrounding tissues and organs, to form lumps and destroy or modify the existing tissue and/or organic structure, and the cancer is used interchangeably with the malignancy. The term "anticancer" means all the activity for inhibiting proliferation of cancer cells or killing the cancer cells. In the present invention, the "blood cancer" is one selected from a group consisting of lymphoma, acute leukemia, chronic leukemia and multiple myeloma, but are not limited thereto. The term "metastasis" means the spread of cancer cells, especially cancer cells associated with blood cancer, from one organ or part thereof to surroundings thereof or another organs, but is not limited thereto. Malignant cancer cells mainly have the ability for metastasis. Cancer cells exit from a primary cancer to the lymph system or blood system, circulate the blood vessels and grow in the normal tissues at other parts of the body. Cancer metastasis, as a typical feature of malignant cancer, is accounted for 90% of deaths due to cancer. Therefore, cancer metastasis inhibition in the present invention is used as the means for inhibiting the spread of cancer cells to other organs or the surroundings. In the present invention, the term "prevention" means any activities to suppress or delay onset of cancer or cancer metastasis by the administration of the pharmaceutical composition of the present invention and "treatment" means any action to improve symptoms caused by the cancer and/or cancer metastatic or to change symptoms by the cancer and/or cancer metastatic to more beneficial states.

Tumor-Associated Macrophage (TAM), as macrophages associated with tumor progression and metastasis, is found mostly in periphery of tumor. A method of improving the tumor microenvironment in a way to attack the TAM by immunizing molecules overexpressed by the TAM has been emerged as a new anti-cancer therapy. The TAM, as a M2 macrophage phenotype, has been primarily known to be induced by Th2 cytokines such as IL-4, IL-13 and so on. Actually the TAM secretes angiogenesis stimulating factor and metalloproteinase, and is involved in the signaling pathways that control the action of the tumor stromal fibroblasts to promote proliferation and metastasis of tumor cells.

In the present invention, the term "Interleukin-4 (IL-4)" means cytokines having various immunomodulatory functions secreted from Th2 lymphocytes, eosinophils, mast cells, etc. It has been reported that the IL-4 is found at a higher concentration than normal tissue, in many cancer cells and a large amount of IL-4 is produced in tumor-infiltrating lymphocytes (TILs). Especially, the IL-4 has been known to a representative cytokine which activates the TAM. Accordingly, the IL-4 induces the activation of the M2 macrophage phenotype M2 and thus induces tumor growth, metastasis, angiogenesis and so on.

Also, it is shown that monoacetyldiacylglycerol compounds are capable of inhibiting the activation of STAT-6, and thus the monoacetyldiacylglycerol compounds can be effectively used for the suppression of the blood cancer or the cancer metastasis. The term "STAT-6" of the present invention, as a transcription factor, has been known to play an important role for performing IL-4-mediated Biological response. That is, the activation of STAT6 in the form phosphorylated by IL-4 is followed by the activation of IL-4/STAT-6 signal pathway. The signaling pathway has been known to play an important role in resistance to the cell proliferation/growth and apoptosis. Accordingly, the suppression of the STAT-6 makes an induction of apoptosis and an inhibition of metastasis, and a destruction of the microenvironment for the growth of the cancer tissue, so that the composition of the present invention can be used for remedy and remedy combination effective in the tumor.

In the examples of the present invention, it is shown that i) when U937 cell, A549 cell and Jurkat cell each is treated with IL-4 and EC-18, the phosphorylation of STAT6 is inhibited depending on concentration of EC-18(Experimental Example 1, FIG. 1 and FIG. 2), and ii) when STAT-6 is treated with EC-18 after activating STAT-6 by treating HEK293 cell and A549 cell with IL-4, the activity of STAT-6 is reduced (Experimental Example 2, FIG. 3). In another example of the present invention, it was shown that the secretion amount of IL-4 is reduced depending upon concentration of EC-18, from the observation on the transfer amount of IL-4 in accordance with the concentrations of the EC-18 by enzyme-linked immunosorbent absorption analysis (ELISA), in RBL –2H3 cell (Experimental Example 3, FIG. 4 and FIG. 5), which suggests the monoacetyldiacylglycerol compounds are effective in the treatment of blood cancer or metastasis. In detail, RPMI 8226 cell of bone cancer cell line originating in human body is transplanted into male nude mice and EC-18 of the test substance is administered orally, thereafter the suppression effect of tumor growth is evaluated. At a test substance administration group of 500 mg/kg dose, the tumor volume is statistically significantly decreased, and also weight of the tumor is statistically significantly decreased, as compared to negative control group. Accordingly it is shown that EC-18 suppress the tumor growth (Experimental Example 4, FIG. 6 and FIG. 7), which demonstrates that monoacetyldiacylglycerol compounds are effective for the prevention or treatment of the blood cancer or inhibition of cancer metastasis.

The pharmaceutical composition containing monoacetyldiacylglycerol compounds of the present invention may additionally include conventional pharmaceutically acceptable carriers, excipients, or diluents. The amount of monoacetyldiacylglycerol compounds in the pharmaceutical composition can be widely varied without specific limitation, and is specifically 0.0001 to 100.0 weight %, preferably 0.001 to 50 weight %, more preferably 0.01 to 20 weight % with respect to the total amount of the composition.

The pharmaceutical composition may be formulated into various forms for oral or non-oral administration, for example one selected from a group consisting of tablet, bolus, powder, granule, capsule such as hard or soft gelatin capsule, emulsion, suspension, syrup, emulsifiable concentrate, sterilized aqueous solution, non-aqueous solution, freeze-dried formulation, suppository, and so on. In formulating the composition, conventional excipients or diluents such as filler, bulking agent, binder, wetting agent, disintegrating agent, and surfactant can be used. The solid formulation for oral administration includes tablet, bolus, powder, granule, capsule and so on, and the solid formulation can be prepared by mixing one or more of the active components and at least one excipient such as starch, calcium carbonate, sucrose, lactose, gelatin, and so on. Besides the excipient, a lubricant such as Magnesium stearate and talc can also be used. The liquid formulation for oral administration includes emulsion, suspension, syrup, and so on, and may include conventional diluents such as water and liquid paraffin or may include various such as wetting agent, sweeting agent, flavoring agent, and preserving agent. The formulation for non-oral administration includes sterilized aqueous solution, non-aqueous solution, freeze-dried formulation, suppository, and so on, and solvent for such solution may include propylene glycol, polyethylene glycol, vegetable oil such as olive oil, and ester for syringe injection such as ethyl oleate. Base materials of the suppository may include witepsol, macrogol, tween 61, cacao butter, Laurin and glycerogelatine.

The composition of the present invention can be administered in a pharmaceutically effective amount. The term "pharmaceutically effective amount" is used to refer to an amount which is sufficient to achieve a desired result in a medical treatment. The "pharmaceutically effective amount" can be determined in accordance with type, age and sex of a subject, severity and type of disease, activity of drug, sensitivity to drug, administration time, period and route, excretion rate, and other well known criteria in medical field. The composition of the present invention can be administered alone or with other medicines sequentially or simultaneously, or administered once or several times. Considering all the above factors, it is important to dose the amount that can achieve the maximum effect with the minimum amount with no side effects, which can be readily determined by those skilled in the art. The preferable amount of the composition of the present invention can be varied in accordance with the condition and weight of patient, severity of disease, formulation type of drug, administration route and period of drug. Appropriate total amount of administration per 1 day can be determined by a doctor of related medical filed, and generally 0.001 to 1000 mg/kg, preferably 0.05 to 200 mg/kg, more preferably 0.1 to 100 mg/kg once or several times by dividing in 1 day. The composition of the present invention can be administered to any subject which requires the suppression of blood cancer or cancer metastasis. For example, the composition of the present invention can be administered to not only human but also non-human animal (specifically mammals) such as monkey, dog, cat, rabbit, guinea pig, rat, mouse, cow, sheep, pig, goat, and so on. The composition of the present invention can be administered by conventional various methods, for example, by oral or rectum administration, or by intravenous, intramuscular, subcutaneous or cerebrovascular injection.

As other aspect of the present invention, the present invention provides a health functional food for inhibiting blood cancer or cancer metastasis comprising monoacetyldiacylglycerol compounds of Formula 1 as an active component(s),

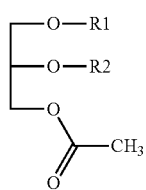

[Formula 1]

wherein R1 and R2 are independently a fatty acid group of 14 to 22 carbon atoms, but are not limited thereto.

In detail, the monoacetyldiacylglycerol compounds of the present invention or pharmaceutically acceptable salt thereof can be included in the health functional food for the suppression of blood cancer or cancer metastasis. The monoacetyldiacylglycerol compounds, suppression of blood cancer or cancer metastasis are previously explained in detail. The term "improving" means every change which reduces or advantageously changes the symptoms in a subject having or suspicious of having blood cancer or cancer metastasis.

When the composition of the present invention is included in the health functional food, the composition can be included alone or with other active component. The amount of the compounds of the present invention in the health functional food can be determined in accordance with the intended use of the health functional food. Generally, when preparing health functional food or beverage, the composition of the present invention can be included in the amount of less than 15 weight part, preferably less than 10 weight part. In case of long term administration for maintaining one's health, the amount of the composition can be reduced. However, since the active component does not cause any adverse effect, the amount of the composition can be increased by more than the above mentioned amount. The health functional food including the composition of the present invention can be any conventional food or beverage. Specific examples of the food include meat, sausage, bread, chocolate, candy, snack, biscuit, pizza, Ramen, noodles, gum, ice cream, dairy product, soup, beverage, tea, drink, alcoholic drink, vitamin complex, and so on. If necessary, the food of the present invention can also include food for an animal.

When the health functional food is beverage, the beverage may include conventional sweetener, flavoring agent, natural carbohydrate, and so on. Examples of the natural carbohydrate include monosaccharide such as glucose and fructose, disaccharide such as maltose and sucrose, polysaccharide such as dextrin and cyclodextrin, and sugar alcohol such as xylitol, sorbitol, and erythritol. The preferable amount of the natural carbohydrate can be about 0.01 to 0.04 g, more preferably about 0.02 to 0.03 g with respect to 100 Ml of the beverage of the present invention. Examples of the sweetener includes natural sweeteners such as Thaumatin and Stevia extract and artificial sweeteners such as saccharin and aspartame. The health functional food of the present invention may further include various nutritional supplement, vitamin, electrolyte, flavoring agent, coloring agent, pectic acid and its salt, alginic acid and its salt, organic acid, protective colloid, thickener, pH adjuster, stabilizer, preservative, glycerin, alcohol, juice and so on.

As another aspect of the present invention, the present invention provides a method for preventing or treating blood cancer or for inhibiting cancer metastasis comprising a step of administering the pharmaceutical composition to a subject who is suspicious of having blood cancer or cancer metastasis. The "subject who is suspicious of having blood cancer or cancer metastasis" includes not only an animal including human being which has blood cancer or cancer metastasis but also potentially has blood cancer or cancer metastasis. The subject who is suspicious of having blood cancer or cancer metastasis can be effectively treated by administering the pharmaceutical composition of the present invention. The term "administering" means introducing the pharmaceutical composition of the present invention into the subject who is suspicious of having blood cancer or cancer metastasis by any means. The administration route can be any route such as oral or non-oral route.

The method for treating blood cancer comprises a step of administering an effective amount of a pharmaceutical composition comprising the monoacetyldiacylglycerol compounds of formula I or pharmaceutically acceptable salt thereof to a patient in need thereof. An appropriate total amount of administration per 1 day can be determined by a physician, and is generally about 0.001 to about 1000 mg/kg, preferably, about 0.05 to 200 mg/kg, more preferably about 0.1 to about 100 mg/kg. The total administration amount per day can be administered once a day or can be administered in divided doses multiple times daily. However, the specific therapeutically effective amount of the monoacetyldiacylglycerol administered to a particular patient can be varied depending on the type and degree of the response to be achieved in the treatment, the specific composition, including whether another agent is included in the composition, the patient's age, body weight, general health status, sex, diet, administration time, administration route, the ratio of composition, treatment period, other drugs used together in the treatment and a variety of factors well known in the medical field.

Effect of Invention

Monoacetyldiacylglycerol compounds of the invention are excellent in the effect of inhibiting the expression of IL-4, and inhibiting the activity of STAT-6, thereby overcoming side-effects of currently used inhibitor for blood cancer or cancer metastasis, while having no toxicity and excellent treatment effect so that Monoacetyldiacylglycerol compounds can be usefully used for the prevention, treatment and improvement of blood cancer or cancer metastasis.

BRIEF DESCRIPTION OF THE DRAWINGS

FIG. 1 presents Western blot analysis in U937 cell, showing phosphorylation inhibitory effect of (A) STAT-6 which is phosphorylated by IL-4, depending on concentration of EC-18 and (B) STAT-6 which is phosphorylated by IFN-γ, depending on concentration of EC-18.

FIG. 2 presents Western blot analysis in A549 cell(A), U937 cell(B) and Jurkat cell(C), showing phosphorylation inhibitory effect of STAT-6 which is phosphorylated by IL-4, depending on concentration of EC-18.

FIG. 3 presents the values of the light-emitting luciferase of STAT-6 which is activated by IL and STAT-1 which is activated by IFN-γ, depending on concentration of EC-18, in HEK293 cell and A54 cell.

FIG. 4 presents the transfer amount of IL-4 depending on concentration of EC-18, in RBL-2H3 cell, which was measured by an enzyme-linked immunosorbent absorption analysis (ELISA).

FIG. 5 shows the expression level of IL-4 over time (6 h, 15 h and 24 h) depending on concentration of EC-18, in RBL-2H3 cell.

FIG. 6 is a graph showing the reduction of tumor volume by the EC-18 treatment in the model animal with which human blood cancer cell are transplanted.

FIG. 7 is a graph showing the reduction of tumor weight by the EC-18 treatment in the model animal with which human blood cancer cell are transplanted.

DETAILED DESCRIPTION OF THE INVENTION

Figure 8:
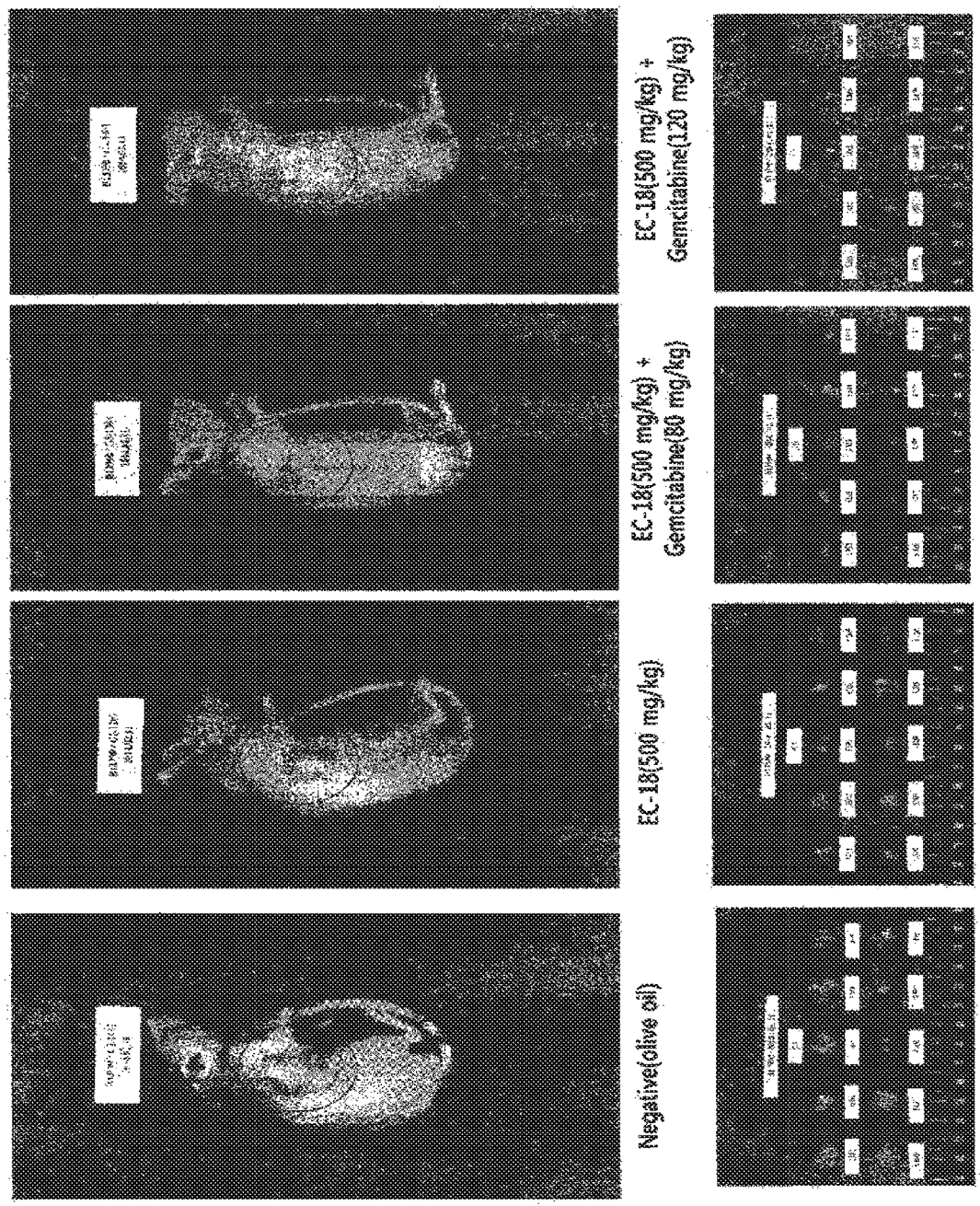
FIG. 8 presents photographs showing the size change of the tumor, in EC-18 treated group, negative control and positive control of blood cancer mouse model.

A more detailed description of the invention will be made by reference to the attached drawings, which are intended for better understanding of the present invention and will not limit the present invention.

Example: Cell Culture

The human cell line U937, A549, Jurkat, HEK293 and rats cell line RBL-2H3 (American Type Culture Collection, ATCC, Rockville, Md.) were cultured at 37° C. under 5% $CO_2$ humid condition. U937, Jurkat, K562 and A549 cell lines were cultured in RPMI1640 (Life Technologies, Karlsruhe, Germany) medium containing 10% elegant serum (Fetal Calf Serum, FCS, HyClone, Logan, Utah), 2 mM L-glutamine, 100 µg/Ml penicillin and 100 µg/Ml streptomycin (Life Technologies), HEK293 cell line was cultured in DMEM medium, and RBL-2H3 cell line was cultured in MEM medium.

Experimental Example 1: Inhibitory Effect of EC-18 on STAT-6 Phosphorylation Cells treated with EC-18 and IL-4 and IFN-γ were lysed with SDS-cold lysis buffer [(50 mM HEPES, 150 mM NaCl, 0.2 mM EDTA, 0.5% NP-40, 0.1% SDS, 1 mM $Na_3VO_4$, 10 mM NaF, and complete Protein Inhibitor Cocktail (Roche)] for 30 minutes on ice. After cell Subsequently, the RNA was isolated after dissolving the cells, the aqueous solution was separated from the insoluble precipitate by centrifuging the cell lysates for 30 minutes at 13,000 rpm in a high-speed centrifuge. After quantifying the separated cell aqueous solution, the quantified solution was separated in 10 to 12% SDS-PAGE by electrophoresis. The cellular proteins separated in the Gel were transferred to PVDF membrane (Millipore, Billerica, Mass., USA) for two hours at 100V.

To measure the amount of phosphorylated STAT1, STAT6 in cells, the membrane was incubated with poly rabbit anti-(STAT1, STAT6), -phosphor (STAT1, STAT6) (Cell signaling Technology, USA) (1:1000) as a primary antibody at room temperature for 60 minutes. The membrane was incubated with horseradish peroxidase peroxidase-conjugated goat anti-rabbit IgG (Santa Cruz Biotechnology, USA)(1:3000) as a secondary antibody at room temperature for 60 minutes. The same amount of cellular proteins was confirmed by poly rabbit anti-(STAT1, STATE) antibody. After incubation with antibodies, membrane was incubated with ECL solution (Millipore, Billerica, Mass., USA) and exposed to X-ray film. The amount of phosphorylated STAT was measured in the band on the film.

The result shows that STAT-6 is phosphorylated in A549 cells of epithelial cells and U937 and Jurkat cells of immune cells, and the amount of phosphorylated STAT-6 is decreased by the pre-treatment of EC-18 in a concentration-dependent manner (FIG. 1-A, FIGS. 2-A to C). FIG. 1B shows that there is no phosphorylation decrease at STAT-1 by EC-18.

Experimental Example 2: Measurement of Inhibitory Effect of EC-18 on STAT-6 Activation Using the Luciferase Reporter The p4×STAT6-Luc2P vector (Addgene) containing the STAT-6 Element (SIE) that STAT-6 binds to was introduced into HEK293 cells and A549 cells. Inhibition of the STAT-6 activation by EC-18 was measured by pre-treating the cells with EC-18 and then treating the cells with IL-4. Also, the activation of STAT-1 was measured by using pGL4.45 [luc2P/ISRE/Hygro] vector (Promega) containing Interferon Stimulated Response Element (ISRE) that STAT-1 binds to.

After disrupting cells by treatment with trypsin-EDTA, HEK293 cells and A549 cells were split to the culture plate. Using Attractene Transfection Reagent (Qiagen), cells were transfected with p4×STAT6-Luc2P and pGL4.45[luc2P/ISRE/Hygro] and and incubated at 37° C. under 5% $CO_2$ conditions for a day. In the next day, the cells were collected from the culture plate and 0.1 ml of cells were transferred to 96-well plate in a concentration of $5 \times 10^4$ cells/well and incubated at 37° C. under 5% $CO_2$ conditions for a day. In the next day, the cells were pre-treated with different concentrations of EC-18 for one hour and then treated with 10 ng/ml of IL-4 and IFN-γ. After incubation at 37° C. under 5% $CO_2$ conditions for 6 hours, Luciferease activity was measured using ONE-Glo Luciferase Assay System (Promega). Specifically, 0.1 ml of a 1:1 mixture of ONE-Glo Luciferase Assay System and Substrate was added to each well. After three minutes, the fluorescence by IL-4 and IFN-γ was measured ONE-Glo Luciferase Assay System (Promega) as follows. Specifically, 0.1 ml of a 1:1 mixture of ONEONE-Glo™ Luciferase Assay Buffer and Substrate was added to each of 96-well. After three minutes, the fluorescence was measured using VICTOR X Multilabel Plate Reader (PerkinElmer) during 0.5 second.

Luciferase fluorescence was decreased in cells pre-treated with different concentrations of EC-18, compared to cells treated with IL-4 alone, indicating decreased STAT-6 activity in cells pre-treated with EC-18. On the other hand, the Luciferase fluorescence of the STAT-1 by EC-18 was maintained in cells treated with IFN-γ (FIG. 3). The result shows that STAT-6 activation induced by IL-4 is decreased by the treatment of EC-18 in HEK293 cells and A549 cells.

Experimental Example 3: IL-4 Gene Expression Inhibitory Effect of the EC-18

Experimental Example 3-1: Reverse Transcriptase Polymerase Chain Reaction (RT-PCR)

After pre-treatment of RBL-2H3 cells with EC-18, cellular activity was induced by antigen for IgE, and as a result, the change in the mRNA levels of the cytokines IL-4 expressed in RT-PCR was performed (Reverse Transcriptase Polymerase Chain Reaction. Total RNA was isolated according to standard protocols, cDNA was synthesized using the AccuScript High Fidelity 1st Strand cDNA Synthesis Kit (Stratagene) according to the manufacturer's instructions. Step 2 RT-PCR reactions were performed using the oligo-dT primer and reverse transcriptase, a primer pair specific and Taq polymerase (Takara, Shiga, Japan). cDNA synthesis of 1 µl was used in PCR reaction of 20 µl constituting 0.5 U Taq DNA polymerase, 1 buffer and 1 mM dNTP mix (Takara) and specific primer pairs.

Amplification by PCR was performed using a GeneAmp PCR system 2700 (Applied Biosystems, Foster city, CA, USA) under the following conditions: 5 minutes at 94°, then 45 seconds at 94°, 45 seconds at 56° and 1 minute at 72°, and then subjected to 25 to 40 cycles). Final extension reaction was carried out at 72° for 7 minutes. Table 1 shows the primer sequences used in the cDNA amplification by PCR. PCR primers were designed using Primer3 program and were purchased from Bioneer, Inc. (Republic of Korea, Daejeon).

TABLE 1

| Name | Forward primer | Reverse primer |
|---|---|---|
| GAPDH | CCATCACCATCTTCCAGGAG (SEQ ID NO: 1) | ACAGTCTTCTGGGTGGCAGT (SEQ ID NO: 2) |
| IL-4 | AATGGGTCTCACCTCCCAAC (SEQ ID NO: 3) | TTCAGCTCGAACACTTTGAA (SEQ ID NO: 4) |

PCR product was separated on a 1.5% agarose gel, stained with ethidium bromide to (ethidium bromide, EtBr), visualized by Gel Doc 2000 UV trans-illuminator (Bio-Rad Laboratories, Hercules, Calif., USA), and then analyzed by using Quantity One software (Bio-Rad Laboratories). Each sample was tested at least three times and data representative was proposed. Cells were pre-treated with 0.01, 0.1, 1.0, and 10 μg/Ml of EC-18 respectively for 1 hour and antigen was processed, and the incubated for 3 hours. Subsequently, the RNA was isolated after cell lysis. CDNA was prepared using reverse transcriptase (reverse transcriptase) with poly A+primers on RNA. The design primers for IL-4 was used in the PCR amplification (Table 1). GAPDH was used as internal standard.

Experimental Example 3-2: Confirmation of IL-4 Secretion Inhibition by Enzyme-Linked Immune abSorbent Assay (ELISA)

The cells were treated with 0.1 μg/Ml to 10 μg/Ml EC-18 for 1 hour and antigen was processed. After the incubation for 18 hours at 37° C., the cell was removed to obtain a supernatant. The quantification of rat IL-4 which was present in the cell culture medium of RBL-2H3 cells was made by carrying out enzyme-linked immunosorbent assay (ELISA) according to the protocol indicated by the manufacturer using commercially purchasable monoclonal antibody (mAb) (BD Biosciences).

As a result, it was confirmed that in the RBL-2H3 cells treated with the EC-18, expression of IL-4 transcript was reduced in proportion to the concentration of the EC-18 (FIG. 4) and expression of the secretion of IL-4 induced by the antigen was reduced in accordance with the EC-18 treatment in the RBL-2H3 cells (FIG. 5). In addition, it was confirmed that the secretion of IL-4 expressed at each time was decreased in a EC-18 concentration-dependent manner, and at 10 μg/Ml concentration of EC-18, secretion of IL-4 was inhibited by up to 60% or more.

Experimental Example 4: Antitumor Efficacy Analysis by EC-18 in Cancer Animal Models The tumor growth inhibition was evaluated after the EC-18 of the test substance was orally administered to male nude mice to which RPMI 8226 cells, derived from a human bone cancer cell lines were transplanted. The experiment included six groups: the negative control group; 500 mg/kg dose of the test substance administration group; the combination group to which 500 mg/kg of the test substance and 80 mg/kg dose positive control substance (gemcitabine, Gemcitabine) are administrated; the combination group to which 500 mg/kg of test substance and 120 mg/kg dose of the positive control substance are administrated; 80 mg/kg dose of positive control group; and 120 mg/kg dose of positive control group. Each group consists of 10 mice. Olive oil an excipient was administered to the negative control group. In test substance administration group, the administration of EC-18 to their stomachs was made once a day for 4 weeks (a total of 28 administrations). In positive control group, the administration of the positive control substance of Gemcitabine) to the abdominal cavity was made twice a week for 4 weeks (a total of 8 administrations). During the observation period, common symptoms were observed once a day, weigh of animal and tumor volume (mm3) in animals were measured twice a week. After the end of the observation period, the tumor was excised and the weight thereof (Tumor weight, g) was measured, the results are shown in FIGS. 6 and 7. As shown in FIGS. 6 and 7, in the test substance administration group of 500 mg/kg dose, the volume of the tumors was significantly suppressed as compared to the negative control group statistically, and the weight of the tumor was also statistically significant small compared to the negative control group so that the growth of tumor was inhibited. Further, in the blood cancer model mice, the photograph showing the change in size of the tumor after administration of the EC-18 and the positive control gemcitabine was shown in FIG. 8. As shown in FIG. 8, it was confirmed that even when the EC-18 was administrated, the size of the tumor was reduced in similar to the positive control.

From the above description, a person skilled in the art will appreciate that the invention may be embodied in other specific forms without changing the technical spirit or essential characteristics. In this regard, the examples described above are intended to be illustrative in all respects and it should be understood as not limiting. The scope of the invention should be understood to include all ranges of the above detailed description and the appended claims, rather than the ranges of the specific examples, as well as all such modifications derived from those equivalents.

What is claimed:

1. A method of reducing a cytokine in a subject comprising:

administering to the subject a monoacetyldiacylglycerol of Formula I:

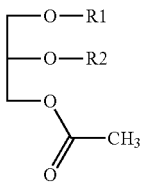

wherein R1 and R2 are independently a fatty acid group comprising 14 to 20 carbon atoms, thereby reducing a cytokine in the subject.

2. The method of claim 1, wherein R1 and R2 are each independently selected from the group consisting of palmitoyl, oleoyl, linoleoyl, linolenoyl, stearoyl, myristoyl, and arachidonoyl.

3. The method of claim 2, wherein R1 is palmitoyl.

4. The method of claim 3, wherein R2 is linoleoyl.

5. The method of claim 1, wherein the cytokine is IL-4, IL-13, or a combination thereof.

6. The method of claim 1, wherein the monoacetyldiacylglycerol reduces secretion of the cytokine from a cell in the subject, inhibits expression of the cytokine in a cell in the subject, or a combination thereof.

7. The method of claim 6, wherein the cell is a cancer cell, a lymphocyte, a leukocyte, or a combination thereof.

8. The method of claim 7, wherein the lymphocyte is a T cell, a tumor-infiltrating lymphocyte, or a combination thereof.

9. The method of claim 7, wherein the leukocyte is a monocyte, an eosinophil, a mast cell, or a combination thereof.

10. The method of claim 1, wherein the monoacetyldiacylglycerol of Formula I is in an amount of 0.001 to 50% by weight of a pharmaceutical composition.

11. The method of claim 10, wherein the pharmaceutical composition is formulated for oral administration.

12. The method of claim 11, wherein the pharmaceutical composition is a capsule, tablet, bolus, powder, or granule.

13. The method of claim 1, wherein the subject is a human or a non-human animal.

14. The method of claim 13, wherein the non-human animal is selected from the group consisting of a monkey, a dog, a cat, a rabbit, a guinea pig, a rat, a mouse, a cow, a sheep, a pig, and a goat.

15. A method of reducing a cytokine in a subject comprising:

administering to the subject a compound of Formula 2:

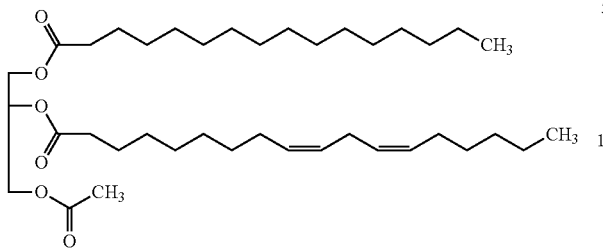

[Formula 2]

wherein the compound of Formula 2 reduces secretion of the cytokine from a cancer cell in the subject, inhibits expression of the cytokine in a cancer cell in the subject, or a combination thereof; and wherein the cytokine is IL-4.

16. The method of claim 1 wherein the subject is a human.

17. The method of claim 1 wherein the cytokine is IL-4.

18. The method of claim 1 further compromising identifying a subject in need of reducing a cytokine and administering the compound of Formula 1 to the identified subject, thereby reducing a cytokine in the subject.

19. The method of claim 15 wherein the administering of the compound of Formula 2 reduces IL-4 in the subject.

20. The method of claim 15 further compromising identifying a subject in need of reducing a cytokine and administering the compound of Formula 1 to the identified subject, thereby reducing a cytokine in the subject.

21. The method of claim 15 wherein the subject is a human.

22. The method of claim 15 further compromising identifying a subject in need of reducing a cytokine and administering the compound of Formula 2 to the identified subject.

23. The method of claim 16 further compromising identifying a subject in need of reducing a cytokine and administering the compound of Formula 2 to the identified subject.

* * * * *